United States Patent
Kuntz

(12) 
(10) Patent No.: US 6,663,631 B2
(45) Date of Patent: Dec. 16, 2003

(54) METHOD AND DEVICE TO CORRECT INSTABILITY OF HINGE JOINTS

(76) Inventor: Charles A. Kuntz, 6651 F Backlick Rd., Springfield, VA (US) 22150

( * ) Notice: Subject to any disclaimer, the term of this patent is extended or adjusted under 35 U.S.C. 154(b) by 245 days.

(21) Appl. No.: 09/987,022

(22) Filed: Nov. 13, 2001

(65) Prior Publication Data

US 2002/0068937 A1 Jun. 6, 2002

Related U.S. Application Data

(60) Provisional application No. 60/250,142, filed on Dec. 1, 2000.

(51) Int. Cl.$^7$ ............................................. A61B 17/56
(52) U.S. Cl. ............................. 606/61; 606/54; 606/70; 606/71
(58) Field of Search ............................. 606/60, 65, 80, 606/61, 62, 63, 54, 69, 70, 71, 86

(56) References Cited

U.S. PATENT DOCUMENTS

| | | |
|---|---|---|
| 4,246,660 A | 1/1981 | Wevers |
| 5,458,601 A | 10/1995 | Young, Jr. et al. |
| 5,492,442 A | 2/1996 | Lasner |
| 5,520,689 A | 5/1996 | Schlapfer et al. |
| 5,527,315 A | 6/1996 | Jeanson et al. |
| 5,540,688 A | 7/1996 | Navas |
| 5,562,660 A | 10/1996 | Grob |
| 5,575,791 A * | 11/1996 | Lin .............................. 606/61 |
| 5,575,819 A | 11/1996 | Amis |
| 5,591,165 A | 1/1997 | Jackson |
| 5,591,166 A | 1/1997 | Bernhardt et al. |
| 5,601,554 A | 2/1997 | Howland et al. |
| 5,620,443 A * | 4/1997 | Gertzbein et al. ............ 606/61 |
| 5,643,260 A * | 7/1997 | Doherty ....................... 606/61 |
| 5,658,283 A * | 8/1997 | Huebner ...................... 606/57 |
| 5,725,527 A | 3/1998 | Biedermann et al. |
| 5,728,127 A | 3/1998 | Asher et al. |
| 5,735,850 A * | 4/1998 | Baumgartner et al. ........ 606/61 |
| 5,928,234 A * | 7/1999 | Manspeizer ................. 606/61 |

FOREIGN PATENT DOCUMENTS

| | | |
|---|---|---|
| FR | 2 679 439 | 1/1993 |
| WO | WO 83/00010 | 1/1983 |
| WO | WO 98/05614 | 6/1989 |

* cited by examiner

*Primary Examiner*—Pedro Philogene
*Assistant Examiner*—David A Bonderer
(74) *Attorney, Agent, or Firm*—Richard C. Litman

(57) ABSTRACT

An orthopedic method and device for correcting instability of an injured hinge joint. The device includes fixed and rotating rigid members connected by a pair of elongated, generally cylindrical shafts. When the device is mounted in place, a single end-threaded pin disposed through the fixed rigid member defines an axis of rotation, allowing the rotating rigid member, which is connected to the rotating member, to go through a range of motion so that the respective joint is not restricted. This motion mimics that of a natural joint and is made possible because the single end-threaded pin is not fixed in place by any structure other than the center-of-rotation bone and the fixed rigid member in which it is a supportably nested. The invention can include an operational surgical method for using the device to correct instability in the injured hinge joint.

9 Claims, 5 Drawing Sheets

METHOD AND DEVICE TO CORRECT INSTABILITY OF HINGE JOINTS

CROSS-REFERENCE TO RELATED APPLICATION

This application claims the benefit of U.S. Provisional Patent Application Ser. No. 60/250,142, filed Dec. 1, 2000.

BACKGROUND OF THE INVENTION

1. Field of the Invention

The present invention relates generally to medical devices. More specifically, the invention is an orthopedic device for stabilizing articulations of body portions in humans or animals, and particularly to a method and device for correcting instability of a hinge joint in a minimum of time.

2. Description of Related Art

Numerous devices have been made for improving the stability of injured parts of the body. Some of the most significant advances in the art have concerned the development of improved apparatus for protecting and supporting injured joints. However, none of the references herein described presents a method and device for correcting instability of articulations, wherein an extracapsular technique is used with fixation through the center of rotation, and wherein no implant is left in place once healing has been completed.

U.S. Pat. No. 4,246,660, issued on Jan. 27, 1981, to Henk W. Wevers, describes a prosthetic ligament device including an elastic element securable to the underlying bone structure by means of a quick release bayonet-type fitting which permits rotational movement during engagement at one end and a length adjusting means at the other end thereof.

U.S. Pat. No. 5,458,601, issued on Oct. 17, 1995, to Franklin A. Young, Jr. et al., describes an adjustable ligament anchor for attaching a ligament to a bone. The ligament anchor includes a housing having an exterior surface, an interior surface, an intra-articular end, and an opposite extra-articular end. The interior surface defines a bore that extends longitudinally through the housing, joining the ends.

U.S. Pat. No. 5,492,442, issued on Feb. 20, 1996, to Jeffrey I. Lasner, describes a bone screw having a helical thread with a constant outside diameter curling around a tapered core. The fine screw tip and thread at the tip of the screw can be inserted into a bone with minimal tearing or cracking of the bone.

U.S. Pat. No. 5,520,689, issued on May 28, 1996, to Johannes F. Schlapfer et al., describes an osteosynthetic fastening device, preferably in the form of a pedicle screw or a spinal column hook, having a channel in its upper section for receiving a support rod, and a retaining element which clamps the rod in the socket through a spherical contact element.

U.S. Pat. No. 5,527,315, issued on Jun. 18, 1996, to Jean-Francis Jeanson et al., describes a device for spinal osteosynthesis, which includes an elongated bar having two parallel, spaced longitudinal slots extending parallel to the bar length. The slots define a central bar branch and two side bar branches flanking the central branch. A plurality of fasteners extend from the bar. Each fastener has a shank to be implanted. A head is provided at an end of the shank. A groove is provided in the fastener head.

U.S. Pat. No. 5,540,688, issued on Jul. 30, 1996, to Fernand Navas, describes an intervertebral stabilization device made in the form of a damper adapted to resist elastically. On the one hand, there is an elongation and, on the other hand, an axial compression without buckling, as well as of at least two implants anchored on two adjacent vertebrae.

U.S. Pat. No. 5,562,660, issued on Oct. 8, 1996, to Dieter Grob, describes an apparatus for stiffening and/or correcting part of the vertebral column including at least two screw-shaped retaining devices, each of which is fixed to one of the vertebrae in the affected part of the vertebral column.

U.S. Pat. No. 5,575,819, issued on Nov. 19, 1996, to Andrew Amis, describes an artificial ligament for connecting across a skeletal joint, including a bundle of fibers, each bundle being made up of a plurality of filaments of polyethylene terephthalate. Also disclosed is a ligament fixation device in the form of a cylindrical grommet, and a tensioning instrument for use in implanting an artificial ligament.

U.S. Pat. No. 5,591,165, issued on Jan. 7, 1997, to Roger P. Jackson, describes a device having a connection element between a rod, or other longitudinal implant, and a bone anchorage screw in the degenerative vertebra. This connection element includes a ring so dimensioned that the rod is capable of extending therethrough. The ring is provided with screws for clamping to the rod and is radially extended by a cylindrical arm adapted to be secured to the bone anchorage screw and to be clamped on the screw.

U.S. Pat. No. 5,591,166 issued on Jan. 7, 1997, to Andrew Bernhardt shows an orthopedic bone bolt and bone plate construct including a bone plate member with open portions and a series of multi-angle fasteners attachable to the bone plate member at the open portions.

U.S. Pat. No. 5,601,554, issued on Feb. 11, 1997, to Robert S. Howland et al., describes a branch connection for spinal fixation systems. The connector comprises a cross brace, upper saddles and connectors for connecting the upper saddles and cross brace to the first and second spine rods to thereby cross brace the first and second spine rods. Lower saddles are integrally formed at opposite ends of the cross brace to mate with the upper saddles in gripping the spine rods.

U.S. Pat. No. 5,620,443, issued on Apr. 15, 1997, to Stanley Gertzbein et al., describes an anterior screw-rod connector device comprising a transverse fixator assembly for spanning between a number of longitudinal members situated adjacent a patient's vertebrae, and methods for fixation of the spine which allow for variation of the distance between two or more vertebrae.

U.S. Pat. No. 5,725,527, issued on Mar. 10, 1998, to Lutz Biedermann et al., describes an anchoring member comprising a shaft to be fastened to a bone and a head for connection with a rod. The head has a substantially U-shaped cross-section and is connected with the shaft at the base thereof. The head further includes two free legs defining a channel for receiving the rod.

U.S. Pat. No. 5,728,127, issued on Mar. 17, 1998, to Marc A. Asher et al., describes an apparatus for maintaining vertebrae of a spinal column in a desired spatial relationship comprising a longitudinal member extendable along the spinal column. A fastener and a staple connects the longitudinal member to a vertebra.

U.S. Pat. No. 5,735,850, issued on Apr. 7, 1998, to Walter Baumgartner et al., describes a fastening system for pedicel screws anchorable in different vertebra. The spherical screw heads lie in spherical shells of apertured counterbodies. The counter-bodies have planar support surfaces which lie on a supporting link in the region of elongate holes.

International Patent Application No. WO 83/00010, published on Jan. 6, 1983, for Jules S. Shapiro, describes a method of fixation of two bone portions, including the steps of holding the bones together, placing a powder fastening device over the bone portions, and activating the fastening device to drive a fastener into the bone portions.

International Patent Application No. WO 89/05614, published on Jun. 29, 1989, for Jean Collomb, describes a synthetic ligament for knees made of a biocompatible material, including an active ligamentary part arranged between the femoral and tibial regions of intra-articular penetration.

French Patent Publication No. 2,679,439, published on Jan. 29, 1993, for Philippe Lepinay describes a quadrilaterally-shaped device for the consolidation and replacement of a ligament.

None of the above inventions and patents, taken either singly or in combination, is seen to describe the instant invention as claimed.

SUMMARY OF THE INVENTION

The present invention is directed to an orthopedic device for stabilization of damaged hinge joints, and includes fixed and rotating rigid members connected by a pair of elongated, generally cylindrical shafts. The shafts allow the device to be adjustable to some extent with respect to the joint over which they expand and, once positioned, are fixed in place by set screws. A single end-threaded and center-of-rotation fixation pin is nested in an aperture disposed through the fixed rigid member, while the rotating rigid member has a pair of apertures, each dimensioned for receiving an end-threaded complementary rotating member or bone fixation pin. When the device is mounted in place, the single end-threaded center-of-rotation fixation pin provides an axis of rotation coincident with its longitudinal axis, so that the rotating rigid body is thereby able to go through a range of motion such that the joint is not restricted. This arcuate motion is made possible because the single end-threaded pin is not anchored in place by any structure other than the bone which has a center of rotation defined and the fixed rigid member in which it movably nests. In contrast, the rotating member includes a pair of set screws, insertably received by apertures disposed through its body to hold it securely in place.

The invention can include an operational method for correcting instability in hinge joints using an orthopedic device for stabilizing hinge joints including the steps of:

(a) placing a single end-threaded pin from medial to lateral or vice versa through the center of rotation; and (b) using the device to guide placement of other fixation pins in the complementary rotating bone or rotating member.

Accordingly, it is a principal object of the invention to provide an orthopedic method and device for correcting instability of various articulations of the body.

It is another object decks line of the invention to provide a joint stabilizing device which leaves no implant in place after healing.

It is a further object of the invention to provide a joint stabilizing device which uses fixation through the center of rotation.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is directed to a method and device for correcting instability in the hinge joints of humans and animals as depicted in FIGS. 1–5 as an orthopedic device 10.

Ligamentous injuries in hinge joints, particularly the collateral ligaments of the elbow and wrist in humans and the hock or tarsal joint in digitigrade quadruped animals, together with prolonged immobilization often significantly result in permanent arthritis. The present invention counteracts this problem by allowing continued range of motion of the damaged hinge joint and reduces the incidence of arthritis.

Figure 1:
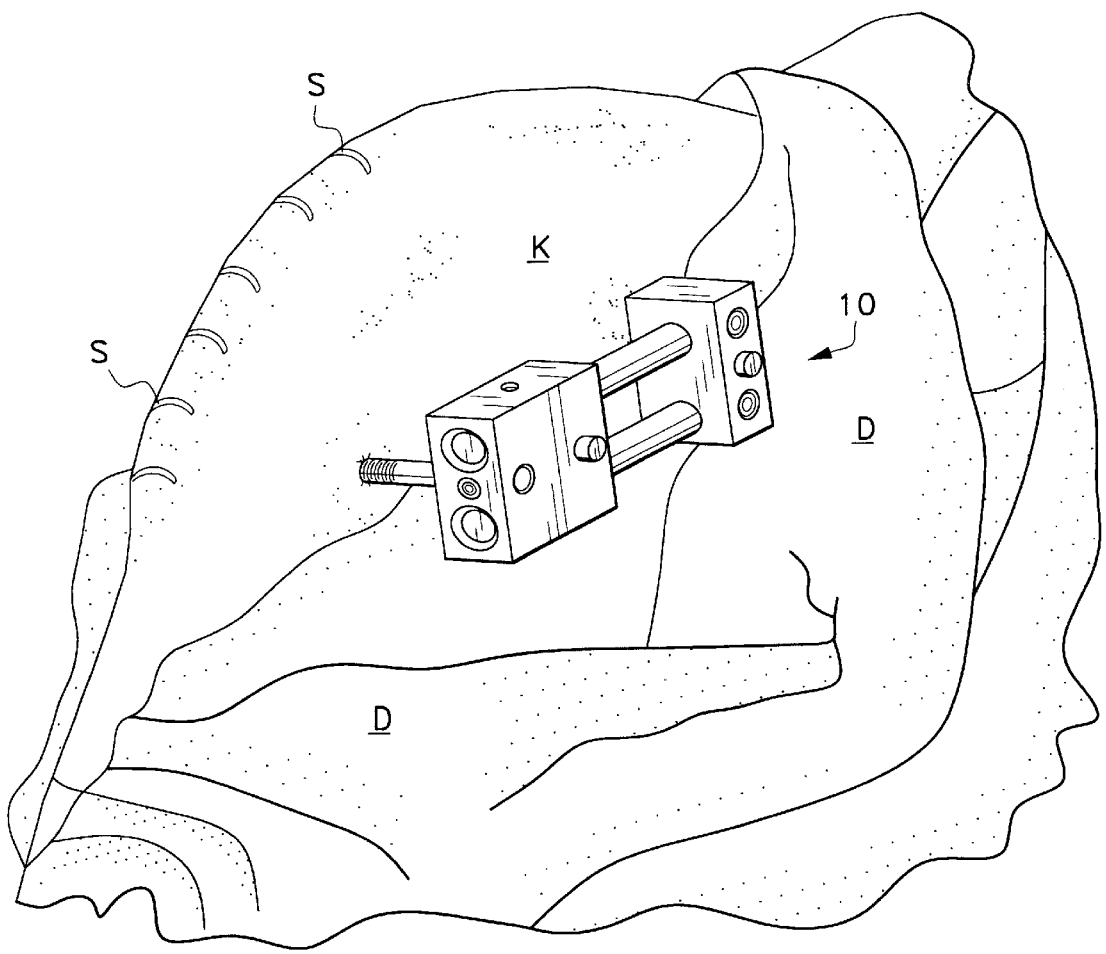
FIG. 1 is an environmental, perspective view of the method and device to correct instability of the canine knee according to the present invention.

It should be emphasized that a longfelt need exists for a more effective way of correcting instability in many kinds of joints, both large and small. The present invention is a response to this need and, when in place, such as shown in FIG. 1, can be used to prevent the displacement of many different types of associated skeletal structures. It should be understood that other surgical approaches can used with the orthopedic device 10, depending on the needs of the patient and the type of joint. A surgical drape is shown at D, the device 10 partially overlying the drape D. The device 10 importantly provides an extracorporeal technique, wherein the bulk of the device 10 is located outside of the patient's hinge joint or knee K.

Figure 4:
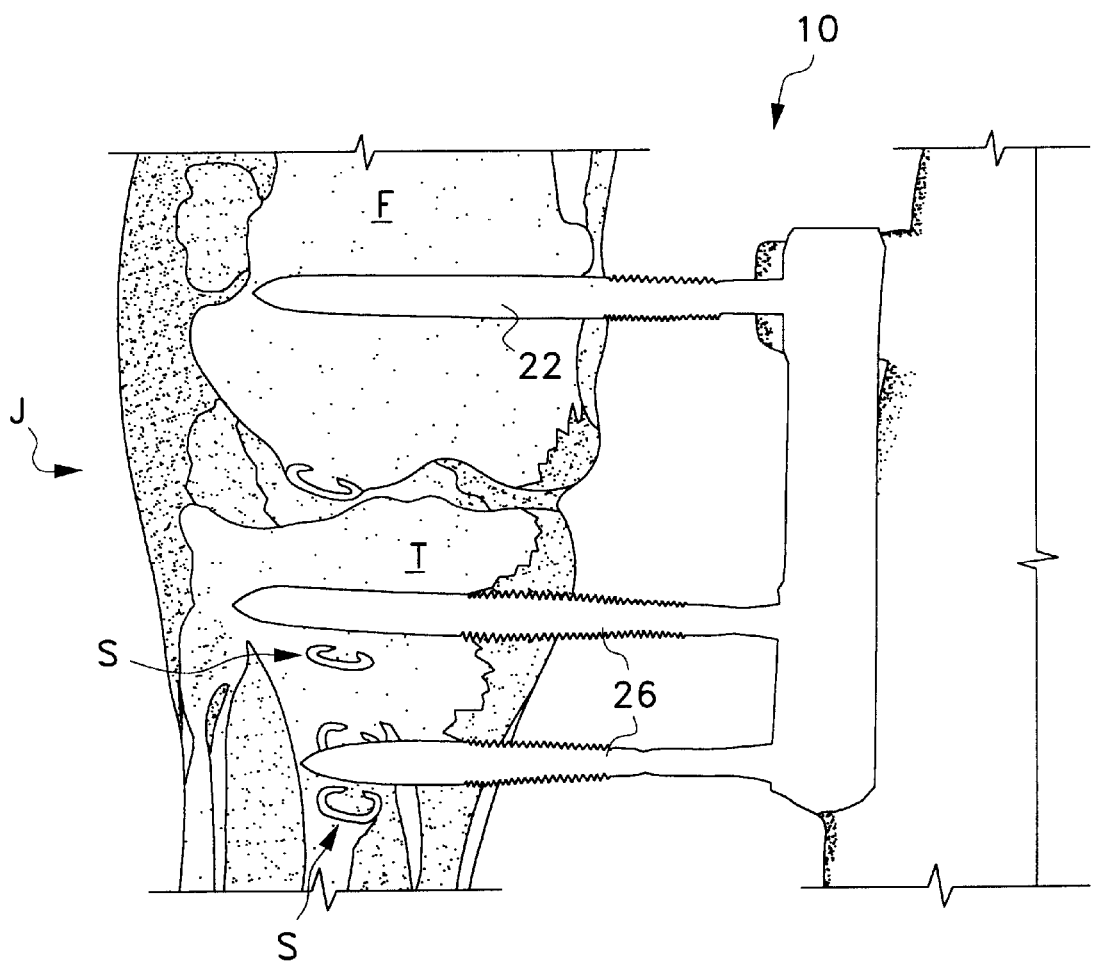
FIG. 4 is a schematic drawing showing how a radiograph might present placement of the device to correct instability of the canine knee, according to the present invention.

The radiographic image of FIG. 4, provides a clearer representation of how the device 10 prevents movement of the tibia or rotating member T relative to the femur or the center of rotation bone F in all directions except hinge-type motion. It is important to emphasize that because the device 10 allows for some natural movement of the injured joint J after placement, it provides a significant advance in the treatment of both humans and animals. Staples for closing the incision are represented at S in FIGS. 1 and 4.

Figure 2:
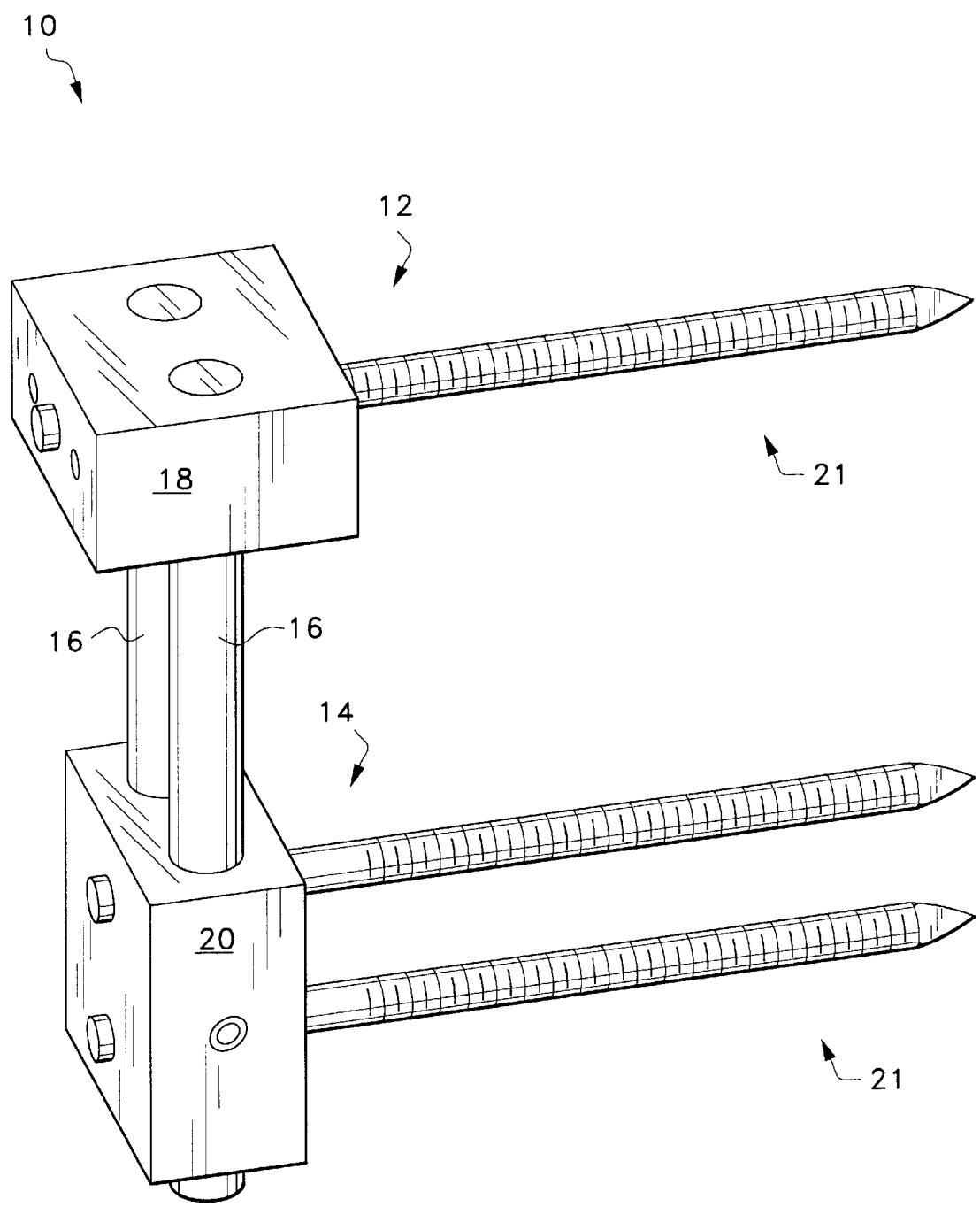
FIG. 2 is a perspective side view of the device to correct instability of the canine knee, according to the present invention.

In FIG. 2, the orthopedic device 10 for correcting instability should provide a significant increase in this rate of surgical success, because the joint J will be able to undergo a range of motion and not be restricted as in conventional methods. The invention principally is made up by fixed 12 and rotating 14 rigid block portions connected by a pair of elongated, generally cylindrical shafts 16. Each shaft 16 is dimensioned for being insertably received through a pair of channels disposed through first 18 and second 20 block members, corresponding to the fixed 12 and rotating 14 rigid block portions, respectively. The substantially cylindrical shafts 16 allow the device 10 to be adjustable to conform with the size of the particular joint by sliding the block members 18 and 20 closer together or farther apart, as needed. Also seen in FIG. 2 are the fixation pins 21.

Figure 3:
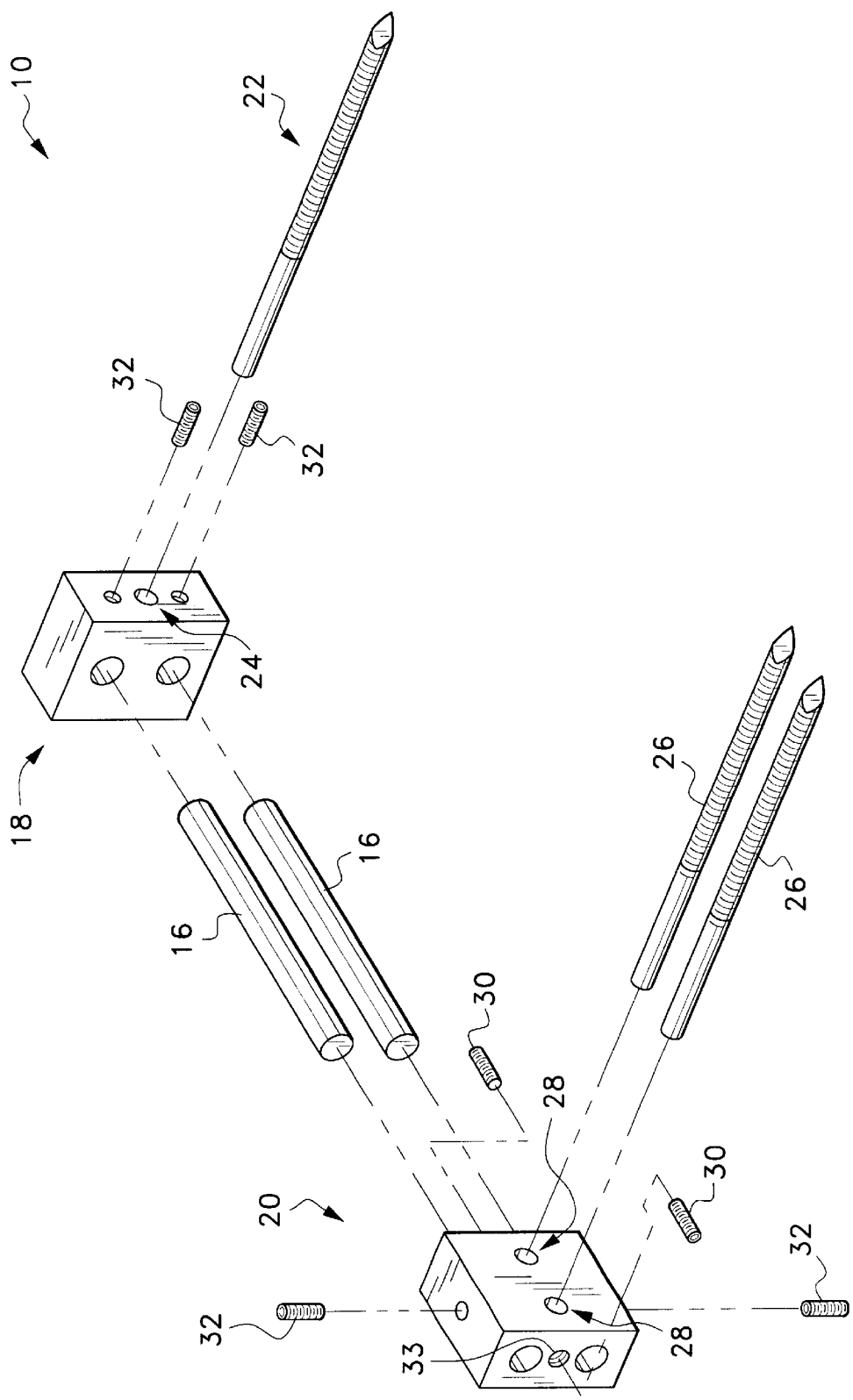
FIG. 3 is an exploded view of the device to correct instability of the canine knee, according to the present invention.

With reference to the exploded view of FIG. 3, where the relationship of the various components and functions of the device 10 can be more fully appreciated, it can be seen that a single end-threaded fixation pin 22 is insertably received by an aperture 24 disposed through the first member 18. In comparison, the second block member 20 employs two end-threaded rotating member fixation pins 26, also insertably received through a respective pair of apertures 28.

When the device 10 is mounted in place, the single end-threaded fixation pin 22 defines an axis of rotation coincident with its longitudinal axis, allowing the second block member 20 to rotate with respect to the first block member 18, and permits the joint to go through a range of motion so that it is not locked down. This more natural motion is made possible because the single end-threaded pin 22 is not held in place by any structure other than the first block member 18 in which it merely nests, so that pin 22 is rotatable in aperture 24. In contrast, the second block member 20 includes a pair of set screws 30, insertably received by apertures 33 (only one shown in FIG. 3, the other aperture being symmetrically disposed on the opposite side of the block member 20) disposed through the body of the second block member 20 to selectively and securely hold the rotating member fixation pins 26 in place.

The end of each cylindrical shaft 16 is also made adjustable in relation to its respective supporting block members, 18 and 20, by set screws 32, the free end of each shaft being held in place by a set screw 32 threadably disposed through an nearby aperture. Thus, each shaft 16 is adjustable within its respective channel; the dual shaft feature prevents the first 18 and second 20 block members from twisting relative to each other, further protecting the ligaments and cartilage of the implanted hinge joint.

As previously noted, rupture of ligamentous structures cause instability. After placement of the device 10, scar tissue builds up over time to form a structure which mimics the function of the damaged ligament. This mass of scar tissue prevents abnormal motion from occurring. It has been found empirically that the present device 10 stabilizes joints more effectively than any other device, method or procedure previously employed, and without limiting range of motion principally because the single end-threaded pin 22 is coincident with the center of rotation of the rotating member or tibia T relative to the center-of-rotation bone or femur F. Returning to the radiograph of FIG. 4, which shows the preferred placement of the device 10, if an observer were to pick any point on the rotating member or tibia T and place the hinge joint K through a range of motion, any point on the rotating member or tibia T would remain the same distance from the center of rotation on the femur or the center-of-rotation bone F. Thus, an important advantage is provided in that the device 10 simulates the functioning of a normal hinge joint K.

The fixation pins 21 are generally of elongated cylindrical shape, each having a distal shaft end. The shaft includes a threaded outer surface configured so as to be implantable in the conventional surgical manner into a patient's bony tissue. Pins 21 of various types such as commonly known in the art can be used. Additionally, the first and second members, 18 and 20, are preferably made of a polymeric material, but aluminum or stainless steel can be used.

The method of the invention shown in FIG. 4 are as follows. A surgical incision in the hinge joint K region is performed, allowing for joint exploration (partial or complete) if required and excision or repair of the ligament remnants. Next, the single end-threaded pin 22 is placed from medial to lateral or vice versa through the center-of-rotation bone or femur F, e.g, stifle which is above the hock of a quadruped animal. The articular surfaces are lavaged with physiologic saline solution, and the joint capsule is closed in routine fashion. The device 10 is then placed with the first member 18 on the single end-threaded pin 22. The set screws 32 are used to fasten the fixed 12 and rotating rigid 14 block portions of the device 10 to the shafts 16 approximately 1 cm. to the articular surface of the rotating member bone T. Non-threaded pins are then used to drill guide holes in the rotating member bone through holes in the rotating rigid block portion 14 of the device 10. After the guide holes are drilled, the device 10 is removed and threaded pins 26 are placed through the guide holes in the rotating member T.

Next, the device 10 is replaced on all three fixation pins 20, and the set screws 32 are tightened in a position, whereby the device 10 is approximately 1 cm. from the skin. After the device 10 is placed on the pins 20, instability in the hinge joint or knee K or other articulation is eliminated. The device 10 is left in place until scar tissue forms in about 12 weeks, and then is removed. The repair is absolutely rigid, allowing scar tissue to form quickly and in an organized fashion. After removal of the external repair, there is nothing left internally to break, interfere with motion or to become infected. Because it is attached at the center of rotation, there is no restriction as to range in motion of the hinge joint K.

Figure 5:
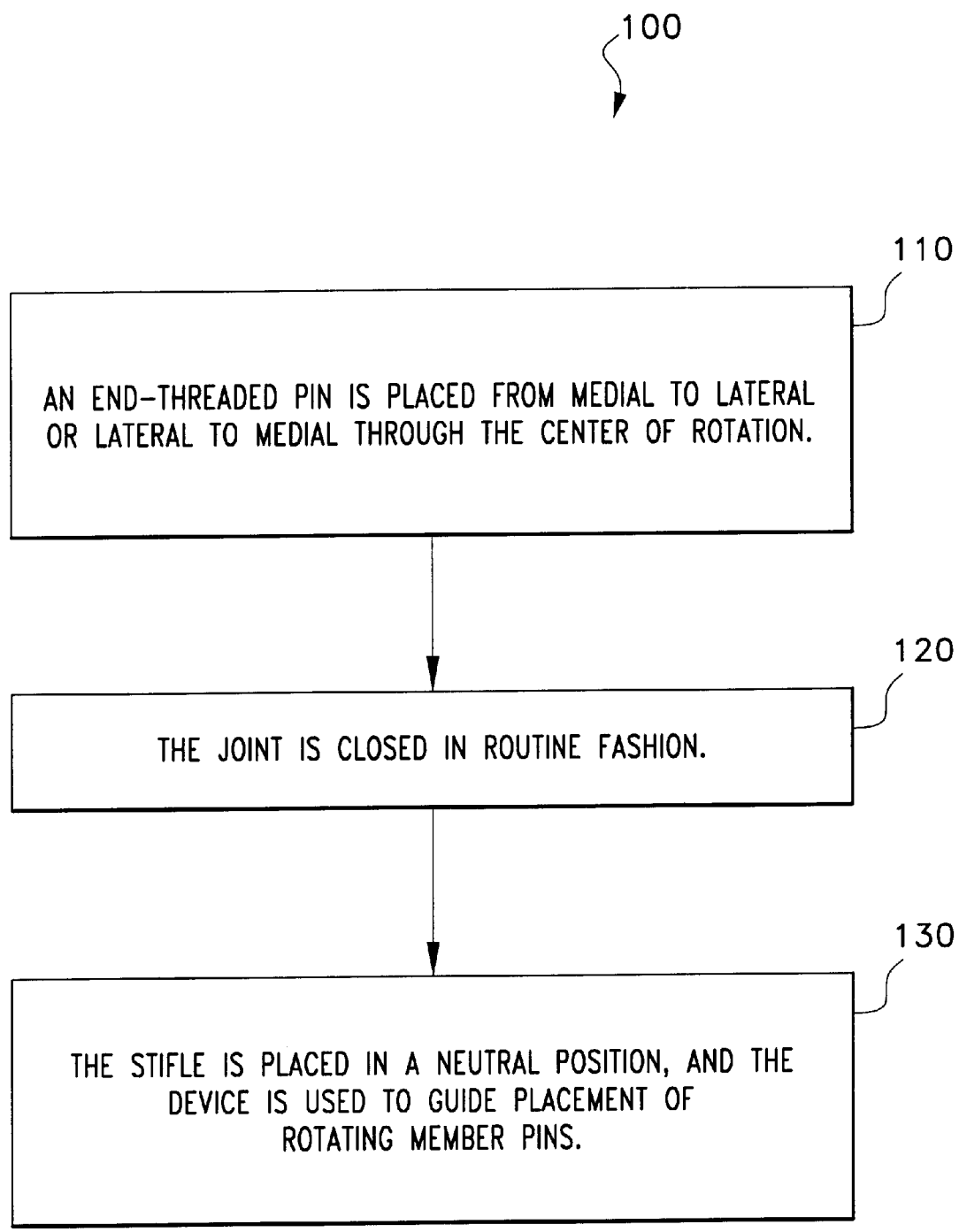
FIG. 5 is a block diagram of the method to correct instability of a canine knee, according to the present invention.

FIG. 5 illustrates the simplified operational method 100 for correcting instability in hinge joints K using the orthopedic device 10 for stabilizing joints in animals and humans in the following brief block steps:

(a) Step 110, placing a first end-threaded pin 22 from medial to lateral or vice versa through the center of the non-rotating bone;

(b) Step 120, surgically closing the joint in routine fashion; and, (c) Step 130, using the device 10 to guide placement of rotating member pins 16 and drilling holes in the rotating bone for placement of the pair of the second end-threaded pins 26.

Thus, it has been shown how an injured hinge joint of animals and humans can be cured in less time with the inventive device employed in the inventive method of application.

It is to be understood that the present invention is not limited to the sole embodiments described above, but encompasses any and all embodiments within the scope of the following claims.

I claim:

1. An orthopedic device, comprising:

first and second rigid block support portions;

a first rigid block portion's fixation pin rotatably mounted in said first rigid block support portion;

a pair of second rigid block portion fixation pins fixedly mounted in said second rigid block support portion;

a pair of shafts interconnecting said first and second rigid block support portions;

said first fixation pin being mountable in a first bony structure on one side of a joint; and said second portion fixation pins being mountable in a second bony structure on an opposite side of the joint, whereby the joint is stabilized by the orthopedic device while the joint is free to articulate about said first rigid portion fixation pin.

2. The device according to claim 1, including at least one fastener for holding each said pair of shafts in place in relation to its adjacent said block support portion.

3. The device according to claim 1, wherein said second block support portion includes a fastener for holding each said second block portion's fixation pin in place.

4. A method for correcting instability in a hinge joint, comprising the steps of:
   (a) providing an orthopedic device, said device including:
       first and second rigid support block portions,
       a first rigid block portion's fixation pin rotatably mounted in said first rigid support block portion,
       a pair of fixation pins fixedly mounted in said second rigid block support portion,
       a pair of shafts, said first and second rigid block support portions being interconnected by said pair of shafts,
       said first fixation pin being mountable in a first bony structure on one side of a joint, and
       said second portion fixation pins being mountable in a second bony structure on an opposite side of the joint, whereby the joint is stabilized by the orthopedic device while the joint is free to articulate about said first rigid portion fixation pin;
   (b) placing said first end-threaded pin from medial to lateral or vice versa through the center-of-rotation bone;
   (c) closing the joint in routine fashion; and,
   (f) using the device to guide placement of the rotating member pins.

5. The method according to claim 4, including further in step (f), the drilling of holes in the rotating bone for placement of the pair of the second end-threaded pins by using apertures in the second block portion as a drilling guide.

6. The method according to claim 5, including insertion of the fixation pins into the drilled holes in the rotating bone.

7. The method according to claim 6, including the attachment of the block portions to all fixation pins.

8. The method according to claim 7, wherein the orthopedic device is adjusted to leave a clearance from the joint.

9. The method according to claim 8, wherein the clearance is at least 1 cm. from the joint.

* * * * *